US00PP28731P2

(12) United States Plant Patent
Henny

(10) Patent No.: US PP28,731 P2
(45) Date of Patent: Dec. 5, 2017

(54) ***ADENIUM* PLANT NAMED 'GEM-113-1'**

(50) Latin Name: *Adenium obesum*
Varietal Denomination: GEM-113-1

(71) Applicant: Richard J. Henny, Tavares, FL (US)

(72) Inventor: Richard J. Henny, Tavares, FL (US)

( * ) Notice: Subject to any disclaimer, the term of this patent is extended or adjusted under 35 U.S.C. 154(b) by 0 days.

(21) Appl. No.: 15/731,646

(22) Filed: Jul. 12, 2017

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen Redden
(74) *Attorney, Agent, or Firm* — James R. Holm

(57) ABSTRACT

A new and distinct *Adenium* plant named 'GEM-113-1' particularly distinguished by having very large flowers averaging 12.0 cm in diameter and averaging 9.0 cm from the petal tips to the base of the floral tube, flowers held erect on the stems when open, a third row of petals expressed in the flowers forming a triple flower, a very large floral tube averaging 3.0 cm in width and 4.0 cm in length, thick stems providing a vigorous and strong appearing growth habit, and large, very dark glossy green leaves, is disclosed.

2 Drawing Sheets

Genus and species: *Adenium obesum.*
Variety denomination: 'GEM-113-1'.

BACKGROUND OF THE NEW PLANT

The present invention comprises a new and distinct variety of *Adenium* plant, botanically known as *Adenium obesum*, and hereinafter referred to by the variety name 'GEM-113-1'. This new *Adenium* plant is the product of a planned breeding program conducted by the inventor in Tavares, Fla. The objective of this breeding program was to create a new plant with triple flowers, strong growth habit, and dark glossy green leaves.

The new variety originated from a controlled cross-pollination made in August 2014 in Tavares, Fla. The female or seed parent was an *Adenium* plant designated 'GEM-97-1' (unpatented), and the male or pollen parent was an *Adenium* plant designated 'GEM-71-2' (unpatented).

The new variety was selected by the inventor as a single plant within the progeny of said controlled cross-pollination in a controlled environment in Tavares, Fla. in October 2014. After selecting the new variety, the inventor continued confidential testing and propagation by apical stem cuttings for a 2-year period in Tavares, Fla. to assess the stability of the new variety's distinctive characteristics. 'GEM-113-1' has been found to retain its distinctive characteristics and has been found to be stable and reproduce true-to-type through successive generations of asexual reproduction by apical stem cuttings.

Plant Breeder's Rights for this variety have not been applied for. 'GEM-113-1' has not been made publicly available or sold anywhere in the world more than one year prior to the filing of this application.

SUMMARY OF THE INVENTION

The new *Adenium* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Adenium* variety when grown under normal horticultural practices in Tavares, Fla. The combination of these characteristics distinguishes 'GEM-113-1' as a new and distinct variety of *Adenium:*

1. Very large flowers, averaging 12.0 cm in diameter and averaging 9.0 cm from the petal tips to the base of the floral tube, flowers held erect on the stems when open;
2. A third row of petals expressed in the flowers forming a triple flower;
3. A very large floral tube averaging 3.0 cm in width and 4.0 cm in length;
4. Thick stems providing a vigorous and strong appearing growth habit; and
5. Large, very dark, glossy green leaves.

DESCRIPTION OF THE PHOTOGRAPHS

This new *Adenium* is illustrated by the accompanying photographs which show the overall plant habit including flowers and foliage of the plant. The colors shown are as true as can be reasonably obtained by conventional photographic procedures. The photographs are of 10-month old plants grown in a non-publically accessible commercial greenhouse in Tavares, Fla. in April 2017. Colors in the photographs may differ slightly from the color values cited in the botanical description which accurately describes the colors of the new variety.

FIG. 1 shows a view of the overall plant habit, including flowers and foliage.

FIG. 2 shows a close-up of a mature flower, branches and leaves.

DESCRIPTION OF THE NEW VARIETY

In the following description, color references are made to The Royal Horticultural Society Colour Chart, 2001 Edition, except where general terms of ordinary dictionary significance are used.

The following observations and measurements describe plants grown in 25 cm containers on raised benches under a clear polyethylene-covered greenhouse in Tavares, Fla. Detailed descriptions were taken from approximately 10-month old plants grown from single apical stem cuttings and pinched one time after rooting. Plants were grown in temperatures ranging from approximately 2° C. to 40° C., and with 20% to 30% shade under a natural photoperiod in Tavares, Fla.

DETAILED BOTANICAL DESCRIPTION

Classification:

*Family*.—Apocynaceae.

*Botanical*.—*Adenium obesum*.

*Common*.—Desert Rose.

*Denomination*.—'GEM-113-1'.

Parentage:

*Female or seed parent*.—*Adenium obesum* plant 'GEM-97-1' (unpatented).

*Male or pollen parent*.—*Adenium obesum* plant 'GEM-71-2' (unpatented).

Propagation:

*Type*.—Apical stem cuttings.

*Time to initiate roots, summer*.—Approximately 21 to 28 days at 20° C. to 30° C.

*Time to produce a rooted young plant, summer*.—Approximately 42 days at 20° C. to 30° C.

Root description: Abundant, thick and well branched, yellow-white in color, RHS 158A and RHS 158B.

Plant description:

*Growth habit*.—Vigorous, strong upright growth, suitable for production as a flowering potted plant in 15 cm containers or larger.

*Caudex*.—Not observed on plants grown from apical stem cuttings.

*Height*.—52.0 cm after 10 months of growth.

*Width*.—40.0 cm after 10 months of growth.

*Growth rate*.—Relatively fast, reaching 52.0 cm after 10 months of growth.

*Stems*.—Diameter of main stem: 3.0 cm. Color: Yellow-green, RHS 148A and RHS 148B. Texture: Smooth. Lateral branches: Quantity: Average 4 on a 10-month old plant pinched one time after rooting. Length: 28.0 cm. Diameter: 1.0 cm to 1.2 cm when measured 10.0 cm below the growing tip. Internodes: Approximately 1.0 cm in length between leaves.

Foliage description:

*Leaf arrangement*.—Alternate.

*Leaf count*.—Approximately 10 leaves per 10.0 cm of stem.

*Average mature leaf size*.—Length: 7.0 cm. Width: 5.0 cm.

*Mature leaf shape*.—Obovate with a mucronate tip measuring 2.0 mm in length.

*Leaf margin*.—Entire.

*Leaf base*.—Leaf base forms a cuneate attachment to the stem.

*Upper leaf surface*.—Smooth in texture, very glossy.

*Lower leaf surface*.—Matte, slightly pubescent.

*Leaf color*.—Mature leaf: Upper surface is green, RHS 139A, lower surface is yellow-green, RHS 146A and RHS 146B. Immature leaf: Upper surface is glossy and lighter green than mature leaves, RHS 137A and RHS 137B, lower surface is yellow-green, RHS 146B.

*Leaf venation*.—Pinnate.

*Petiole*.—Not observed, sessile.

Inflorescence:

*Season*.—Flowers observed year-round in Tavares, Fla., with a larger quantity of flowers observed during the spring, summer and fall months when day and night temperatures are warm.

*Type and habit*.—Axillary compound cyme.

Flowers:

*Longevity*.—5 to 10 days.

*Quantity of buds*.—5 to 6 per stem.

*Quantity of open flowers*.—2 to 5 per 10-month old plant.

*Length*.—9.0 cm when measured from the petal tip to the base of the floral tube.

*Diameter*.—Average 12.0 cm.

*Petals*.—Quantity: 15 per flower in a triple configuration. Length: 9.0 cm. Petaloids: None observed. Texture: Smooth, slightly velvety. Margins: Wavy. Color: Edges are red, RHS 46A and RHS 46B, blending to red-purple, RHS 65A, towards the center, and then blending to white, RHS 155B, near the floral tube throat; as flowers age, outer petal surfaces fade to red, RHS 54A and RHS 54B; the petal's inner surface colors do not fade with age.

*Nectar guides*.—Quantity: 3, present only on the outer whorl of petals, not present on the inner petals. Color: Red-purple, RHS 57B and RHS 57C.

*Floral tube*.—Length: 4.0 cm. Width: Wide, averaging 3.0 cm. Color: Yellow, RHS 2B and RHS 2C.

*Mature buds*.—Shape: Oblanceolate. Length: 7.0 cm. Diameter: 2.0 cm. Color: Lower section: Yellow, RHS 2B and RHS 2C. Tip: Red, RHS 46A.

*Peduncle*.—Length: 0.5 cm. Diameter: 0.6 cm. Color: Yellow-green, RHS 146A and RHS 146B. Orientation: Outward. Strength: Very strong.

*Pedicel*.—Length: 1.0 cm. Diameter: 0.5 cm. Color: Yellow-green, RHS 146A and RHS 146B.

*Sepals*.—Quantity per flower: Approximately 5. Shape: Lanceolate. Length: 1.5 cm. Width: 0.5 cm. Color: Close to yellow-green, RHS 146B. Margins: Entire. Texture: Smooth.

Reproductive organs:

*Stigma shape*.—Club like.

*Style length*.—2.0 cm.

*Style color*.—Yellow-white, RHS 158B.

*Ovary color*.—Yellow-white, RHS 158C.

*Stamens*.—Quantity: 5. Anthers: Shape: Linear. Length: 1.0 cm. Color: Yellow-white, RHS 158B, and blushed with red-purple, RHS 69A. Anther tails: Length: Average 4.0 cm. Color: Red-purple, RHS 69A with darker tips colored red-purple, RHS 67B. Filament length: 1.5 cm. Pollen: None observed.

Fruit and seed set: None observed.

Disease and pest resistance: Normal for this species.

Drought tolerance: Normal for this species.

COMPARISON WITH PARENTAL VARIETIES

'GEM-113-1' differs from the female parent plant 'GEM-97-1' (unpatented) in that 'GEM-113-1' produces triple flowers, whereas 'GEM-97-1' produces double flowers.

Additionally, 'GEM-113-1' has dark red colored flowers, whereas 'GEM-97-1' has white colored flowers. Furthermore, the stems and leaves of 'GEM-113-1' are larger and thicker than the stems and leaves of 'GEM-97-1'.

'GEM-113-1' differs from the male parent plant 'GEM-71-2' (unpatented) in that 'GEM-113-1' has dark red colored flowers, whereas 'GEM-71-2' has light reddish-pink colored flowers. Additionally, 'GEM-113-1' produces triple flowers, whereas 'GEM-71-2' produces single flowers. Furthermore, the stems and leaves of 'GEM-113-1' are larger and thicker than the stems and leaves of 'GEM-71-2'.

COMPARISON WITH KNOWN CULTIVARS

'GEM-113-1' differs from the commercial variety 'LEELADE204' (U.S. Plant Pat. No. 24,833) in that 'GEM-113-1' produces triple red flowers, whereas 'LEELADE204' produces double red flowers. Additionally, mature leaves of 'GEM-113-1' measure 7.0 cm in length and 5.0 cm in width, whereas mature leaves of 'LEELADE204' measure 9.2 cm in length and 3.9 cm in width. Furthermore, flowers of 'GEM-113-1' measure 9.0 cm in length and 12.0 cm in diameter, whereas flowers of 'LEELADE204' measure 8.1 cm in length and 4.1 cm in diameter.

I claim:

1. A new and distinct variety of *Adenium* plant named 'GEM-113-1', substantially as illustrated and described herein.

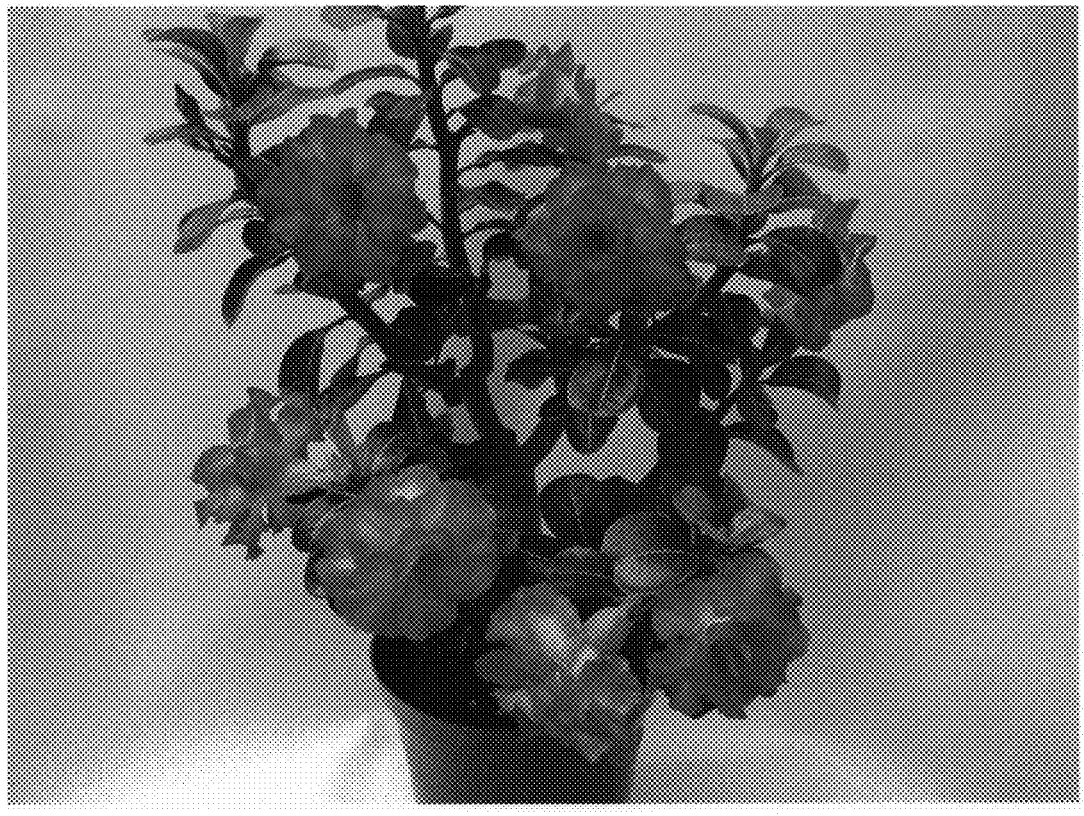

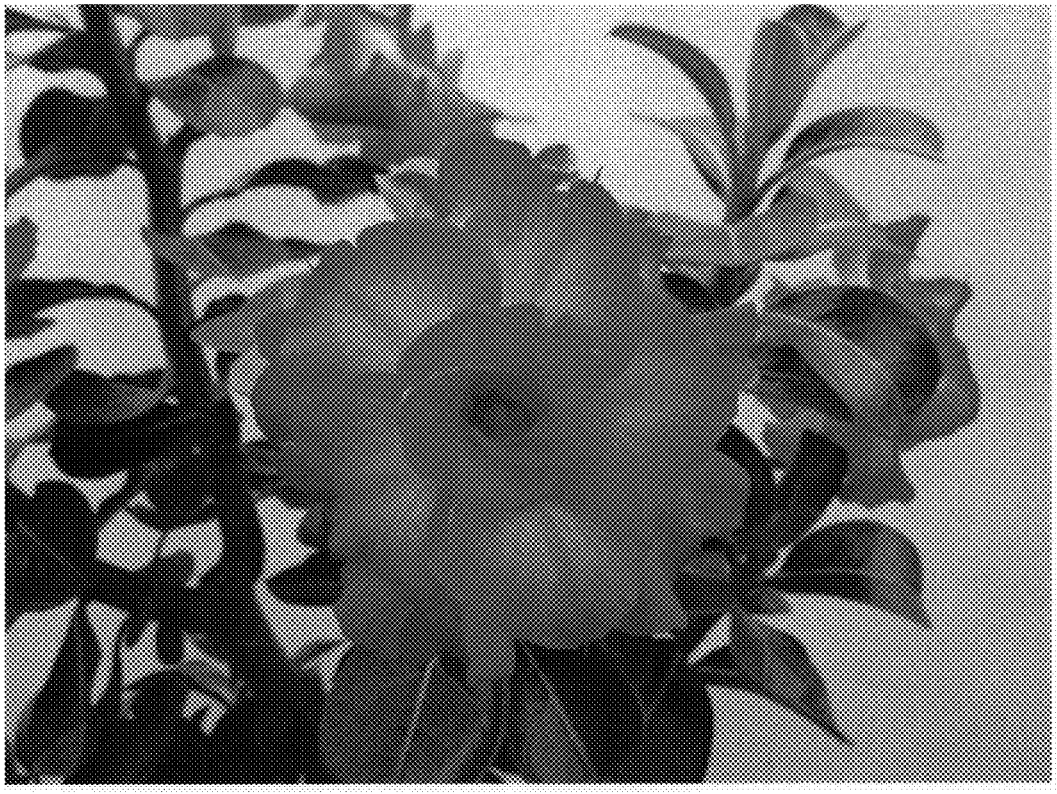

* * * * *